United States Patent
McLean et al.

(10) Patent No.: US 6,510,970 B2
(45) Date of Patent: Jan. 28, 2003

(54) COUPLING ADAPTOR FOR USE WITH AN AIR/WATER SYRINGE TIP OF A FLUID DISPENSING DEVICE

(75) Inventors: Bruce S. McLean, Sandy, UT (US); Wade J. Cannon, Orem, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 1 day.

(21) Appl. No.: 09/871,221

(22) Filed: May 31, 2001

(65) Prior Publication Data
US 2002/0179651 A1 Dec. 5, 2002

(51) Int. Cl.⁷ .............................. B67D 3/00; B65D 25/40
(52) U.S. Cl. ..................... 222/527; 222/567; 239/390; 239/600; 433/80; 433/88
(58) Field of Search .................... 239/289, 390, 239/391, 397, 600, 602; 222/527, 567, 568; 433/80, 88, 90; 604/93.01, 236, 247

(56) References Cited

U.S. PATENT DOCUMENTS

| | | | |
|---|---|---|---|
| 3,745,655 A | | 7/1973 | Malmin ....................... 32/40 R |
| 3,949,748 A | | 4/1976 | Malmin ............... 128/218 DA |
| 4,258,884 A | * | 3/1981 | Rogers ........................ 239/390 |
| 4,768,954 A | * | 9/1988 | Dragon ......................... 433/90 |
| 4,995,540 A | * | 2/1991 | Colin et al. .................. 222/567 |
| 5,049,071 A | * | 9/1991 | Davis et al. .................. 433/80 |
| 5,378,149 A | | 1/1995 | Stropko ........................ 433/80 |
| 5,445,523 A | * | 8/1995 | Fischer et al. ................ 433/90 |
| 5,767,759 A | * | 6/1998 | Bruns et al. ................. 239/600 |
| 5,944,698 A | * | 8/1999 | Fischer et al. .............. 604/247 |

OTHER PUBLICATIONS

Dental Disposables Intetnational; *http://www.dentaldisposables.com/stp.html*, Jul. 17, 2001, 1 page.

* cited by examiner

*Primary Examiner*—Steven J. Ganey
(74) *Attorney, Agent, or Firm*—Workman, Nydegger & Seeley (57) ABSTRACT

A coupling adaptor for use in connecting a delivery tip to an air/water tip of a fluid dispensing apparatus such as a three-way syringe. The coupling adaptor includes a sidewall that extends between a proximal grasping end and an opposing distal coupling end. The sidewall has an interior surface defining a chamber sized so as to enable an air/water tip to be positioned within the chamber. The coupling adaptor may include structure so as to form a compression fit with a delivery tip and/or threaded engagement tip with the delivery tip. The interior surface of the sidewall may be adapted to form a seal with the air/water tip. The coupling adaptor may be formed from a flexible plastic such as polyethylene.

21 Claims, 7 Drawing Sheets

COUPLING ADAPTOR FOR USE WITH AN AIR/WATER SYRINGE TIP OF A FLUID DISPENSING DEVICE

BACKGROUND OF THE INVENTION

1. The Field of the Invention

The present invention relates to a coupling adaptor for use with an air/water tip of a fluid dispensing apparatus known as a "three-way" syringe. The coupling adaptor enables a delivery tip to be coupled with the coupling adaptor.

2. The Relevant Technology

Figure 1:
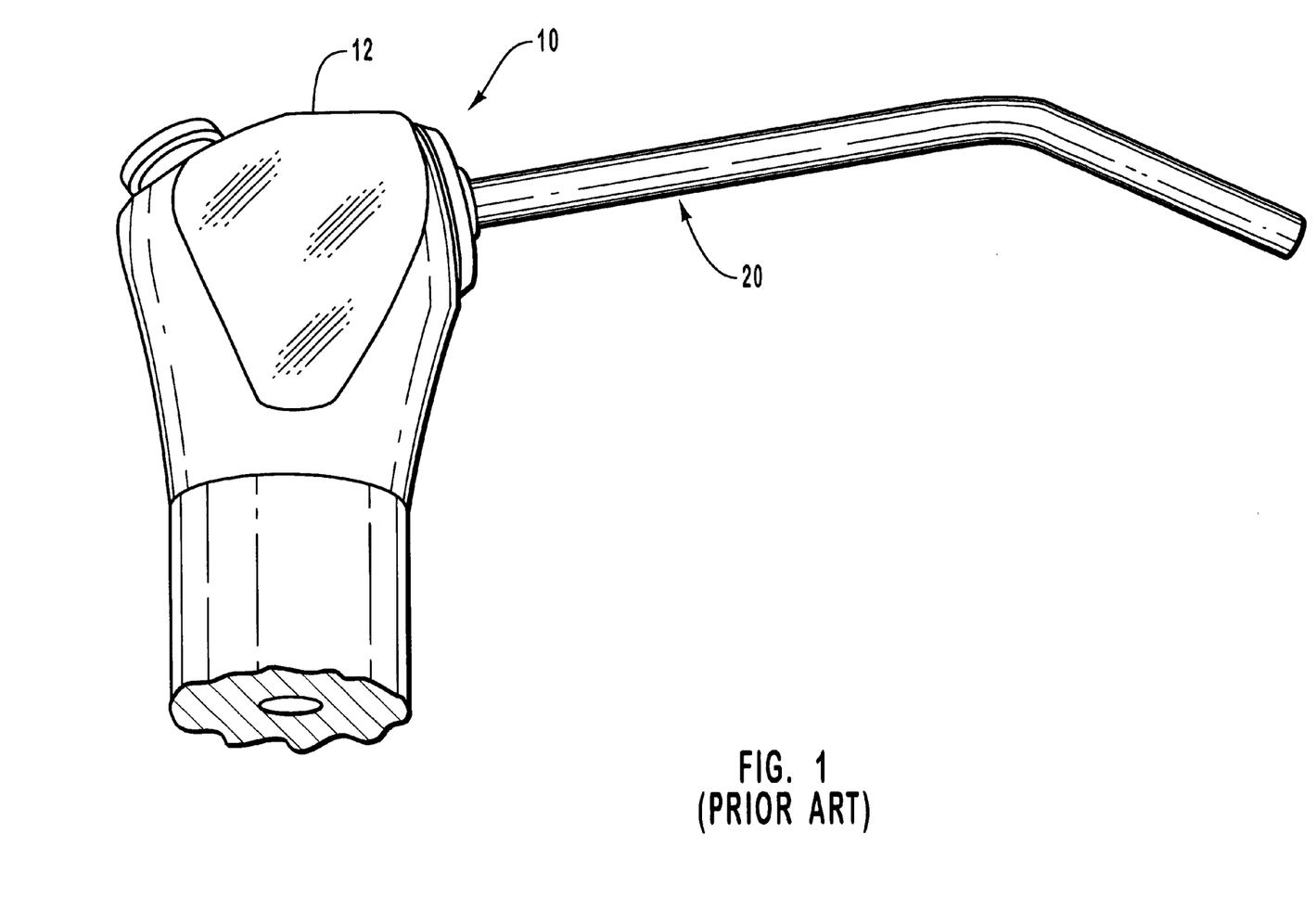
FIG. 1 is a perspective view of a conventional three-way syringe having an air/water tip inserted into a dispensing head.

FIG. 1 depicts a conventional three-way syringe at 10 having a bent air/water tip 20 inserted into dispensing head 12 of three-way syringe 10. The term "three-way" refers to the ability of the syringe to deliver air, water or both. Air/water tip 20 enables the three-way syringe 10 to deliver these fluids in a precise stream. Such syringes can be used in many applications, but are most widely utilized by dentists. For example, dentists often use such devices to deliver air, water or both to a tooth during a restoration process. A problem with the design of conventional air/water tips such as tip 20 is the inability to couple threaded delivery tips that are widely used in dentistry with regular syringes.

Figures 2A, 2B:
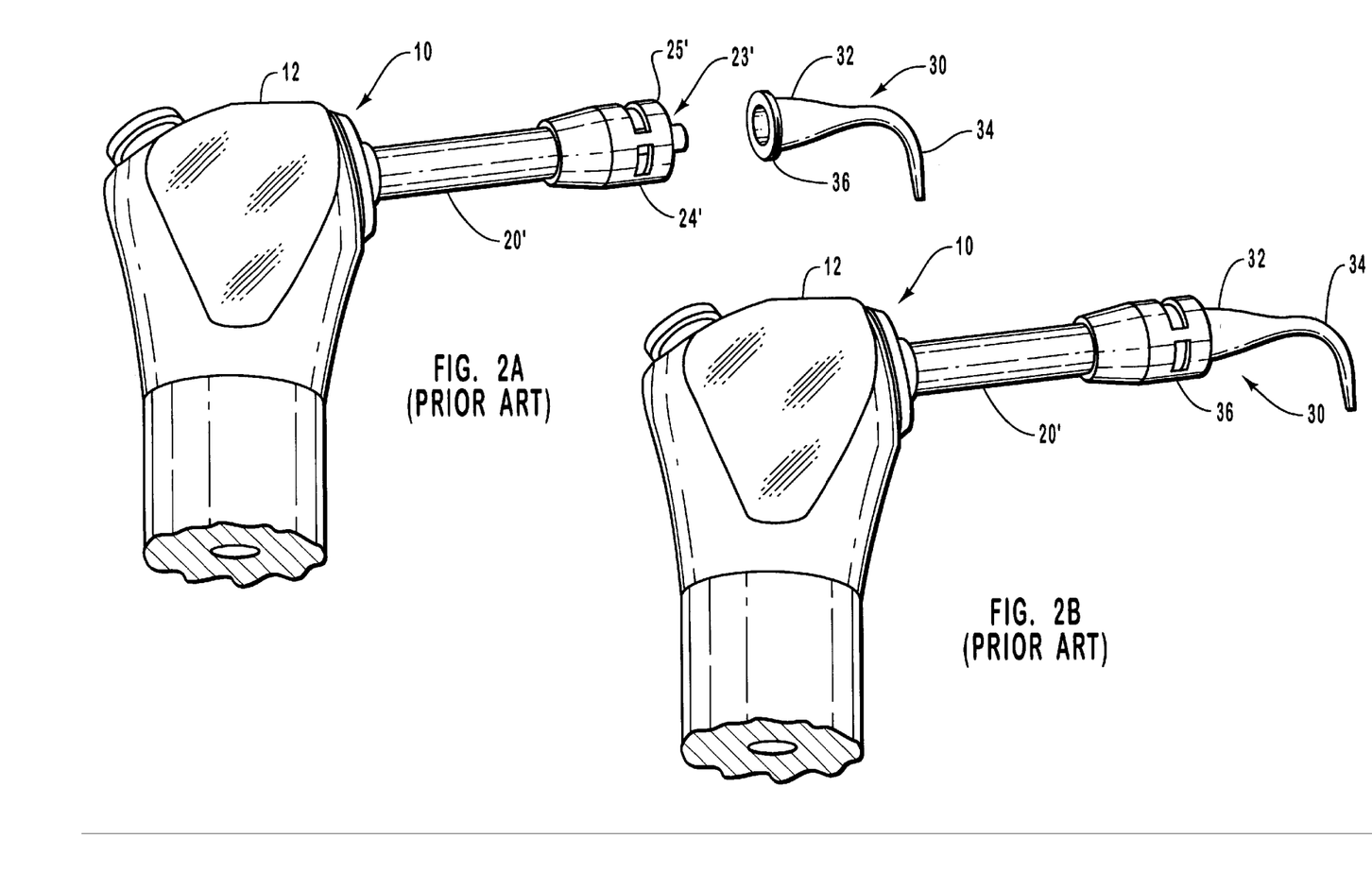
FIG. 2A is a perspective view of conventional three-way syringe having a Stropko-type tip inserted into the dispensing head of the three-way syringe and an endodontic irrigator tip ready for coupling with the Stropko-type tip.
FIG. 2B is a perspective view of the three-way syringe having the endodontic irrigator tip coupled thereto using the Stropko-type tip shown in FIG. 2A.

FIGS. 2A and 2B depict an air/water tip known as a Stropko-type tip 20' that was developed to overcome this problem, as disclosed in detail in U.S. Pat. No. 5,378,149 issued to John J. Stropko, which is hereby incorporated by reference. As shown in FIG. 2A, a delivery tip such an endodontic irrigator tip 30 can be coupled onto the distal delivery end 23' of air/water tip 20'. Delivery tips such as tip 30 typically have a hollow hub 32 at one end and a small bore cannula or a nozzle 34 extending from the hub at an opposite end. The hub 32 typically has a threaded rim 36 adapted to engage the threads (not shown) at distal delivery end 23'. More particularly, threaded rim 36 engages the threads (not shown) on the interior side 25' of skirt 24. FIG. 2B depicts delivery tip 30 coupled in a threaded engagement with air/water tip 20'.

As discussed in detail in U.S. Pat. No. 5,378,149, one of the primary advantages of the Stropko-type tip is that a delivery tip having LUER-LOK® threadings can be coupled to the Stropko-type tip. Another advantage is that Stropko-type tips can be repeatedly autoclaved since they are formed from metal. However, forming the Stropko-type tips from metal results in increased costs. The Stropko-type tips are also relatively expensive due to their numerous components.

Additionally, use of a Stropko-type tips requires that a conventional air/water tip such as tip 20 (FIG. 1) be removed and replaced with a Stropko-type tip 20' (FIGS. 2A and 2B). Switching the tips does not require a significant amount of time. However, it would be very convenient to eliminate the need for substituting a Stropko-type adaptor for a conventional air/water adaptor when coupling with a threaded delivery tip is desired. Additionally, it would be cost effective to eliminate the need for having both a conventional air/water tip and a Stropko-type tip.

Accordingly, what is needed in the art is an adaptor that can work with a conventional air/water tip of a fluid dispensing device such as a three-way syringe to enable a delivery tip to couple with the adaptor in a manner such that the delivery tip and the conventional air/water tip are in fluid communication.

Additionally, what is needed in the art is an adaptor that is inexpensive and easy to use with a conventional air/water tip of a fluid dispensing device such as a three-way syringe.

BRIEF SUMMARY OF THE INVENTION

The present invention provides a coupling adaptor having a flexible sidewall extending between a proximal grasping end and an opposing distal end. The sidewall has an interior surface which defines a chamber. The coupling adaptor also has an opening at the proximal grasping end for accessing the chamber and an exit port at the distal end for enabling the composition to exit the chamber. A grasping handle which extends generally perpendicularly and radially from the sidewall is located at or near the proximal grasping end of the coupling adaptor.

In use, the coupling adapter is inserted over a conventional air/water tip of a fluid dispensing device, such as a three-way syringe. Because the coupling adapter is advantageously flexible, it is able to bend or conform to any bends associated with the air/water tip. The flexible and resilient nature of the sidewall also helps the coupling adapter grip the outer surface of the air/water tip so as to remain in place during use.

A conventional delivery tip may advantageously be attached to the exit port of the distal end of the coupling adaptor so as to provide a desired spray pattern. In a preferred embodiment, the delivery tip will engage the distal end of the coupling adapter in a threadable fashion, e.g., using a LUER-LOK® threading.

The above described syringe and method of use provides several advantages and improvements over the prior art.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings as listed hereinbelow.

DETAILED DESCRIPTION OF THE PREFERRED EMBODIMENTS

The present invention is directed to a coupling adaptor used with an apparatus for delivering fluids, namely air, water and a combination of air and water. More particularly, the present invention is directed to methods and apparatus for delivering such fluids from a fluid dispensing device to a delivery tip.

Figure 3A:
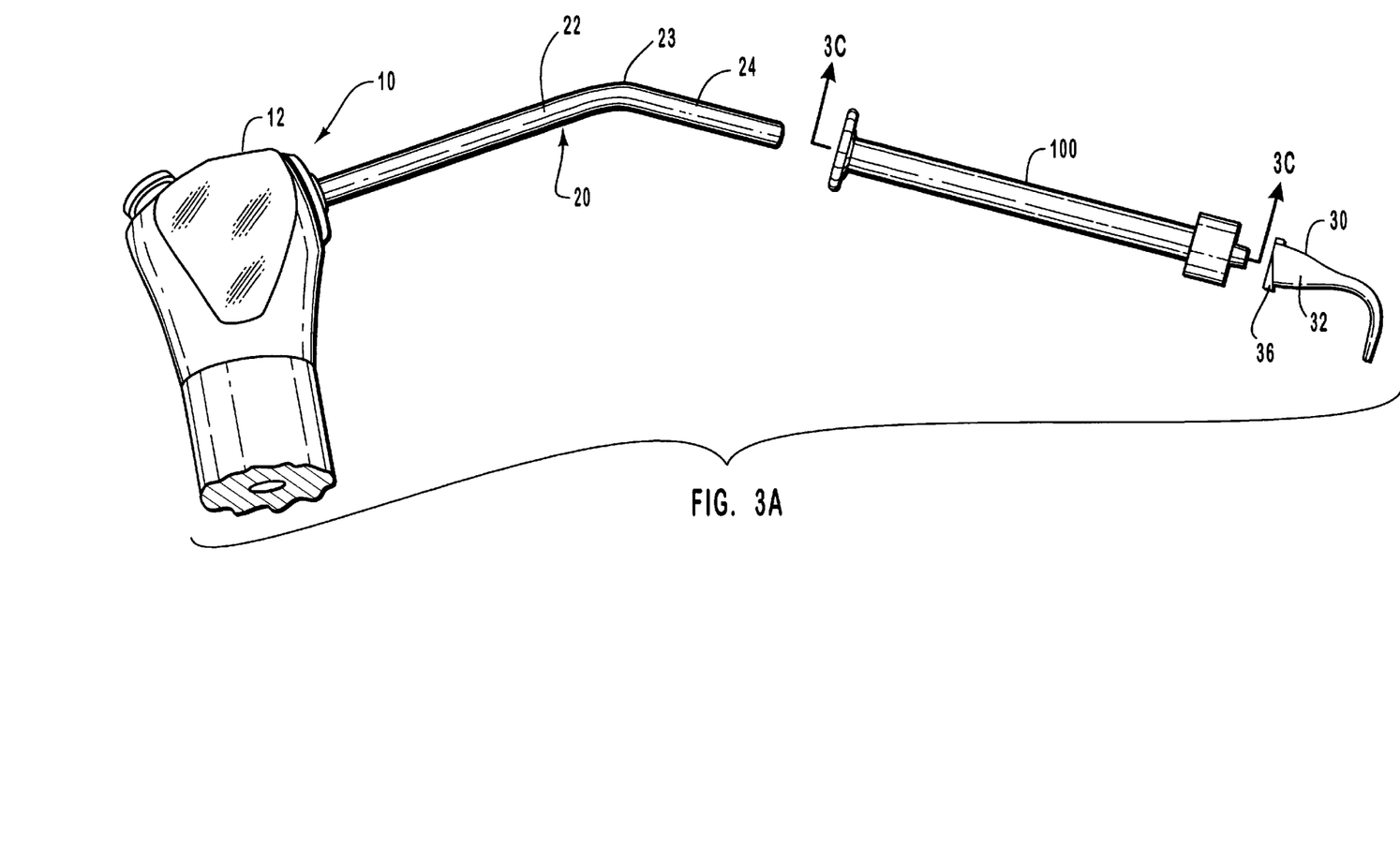
FIG. 3A is an exploded perspective view of a coupling adaptor according to the invention positioned for insertion onto an air/water tip extending from a dispensing head of a three-way syringe and for coupling with an endodontic irrigator tip.
Figures 3B, 3C:
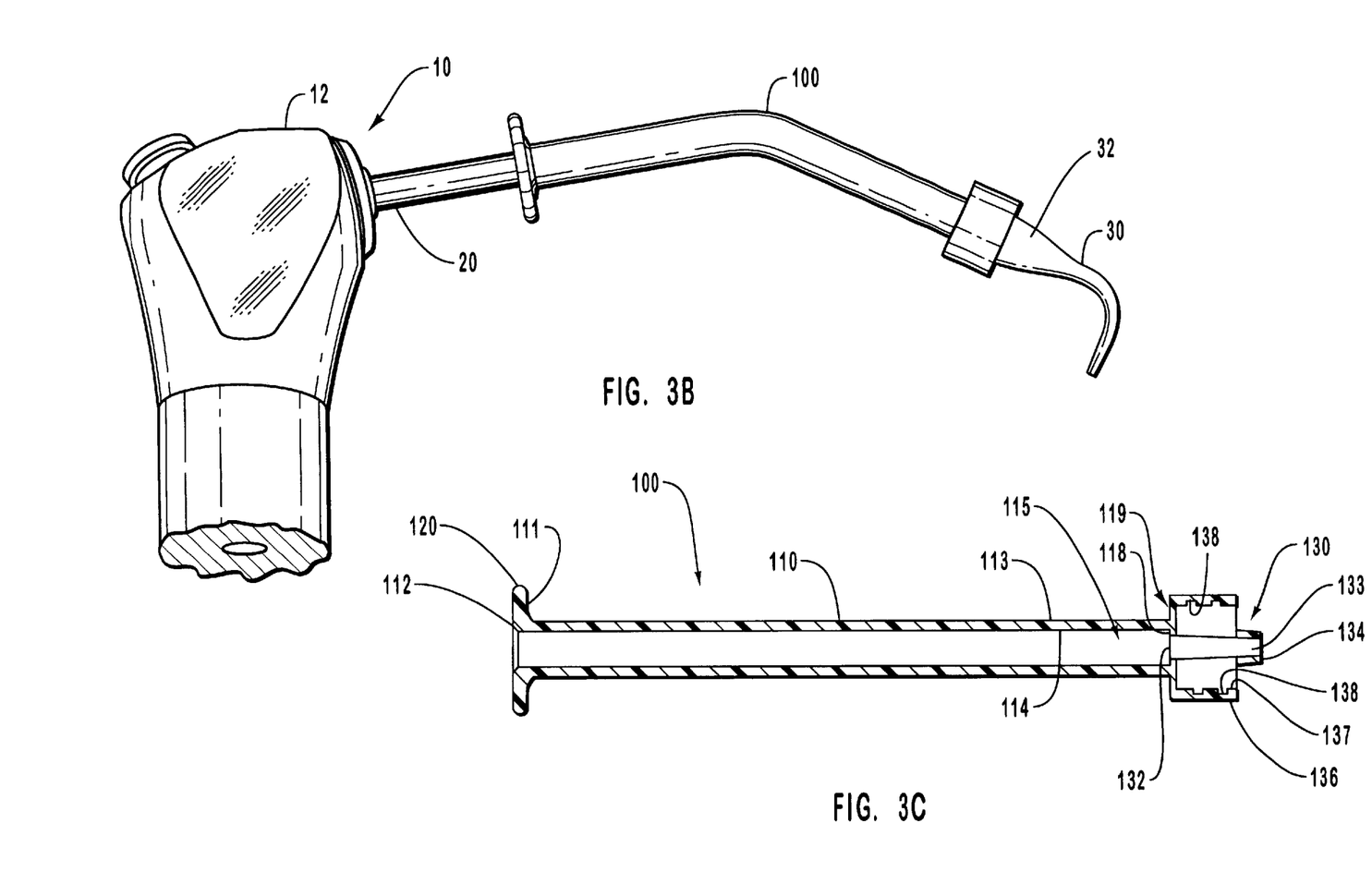
FIG. 3B is a perspective view of the coupling adaptor shown in FIG. 3A positioned on the air/water tip and coupled at a distal end with the endodontic irrigator tip.
FIG. 3C is a cross-section view of the coupling adaptor shown in FIGS. 3A–3B taken along line 3C—3C of FIG. 3A.

FIGS. 3A–3C depict an embodiment of a coupling adaptor 100 adapted for use with a conventional air/water tip 20 of a fluid dispensing device, such as a three-way syringe 10, to enable a delivery tip, such as a threaded delivery tip 30, to couple with the adaptor 100 in a manner so that the delivery tip 20 and the air/water tip 20 are in fluid communication. FIG. 3A shows an exploded perspective view of the air/water tip 20, coupling adaptor 100 and delivery tip 30. FIG. 3B shows these same components assembled such that the modified three-way syringe 10 is ready for use. FIG. 3C is a cross-section view of adaptor 100 taken along line 3C—3C of FIG. 3A.

Coupling adaptor 100 is sized so as to slide onto the air/water tip 20 and is held in place by several features. These features are disclosed below following an explanation of the main features of coupling adaptor 100.

Coupling adaptor 100 has a proximal grasping end 111 opposite a distal coupling end 119 with a substantially cylindrical sidewall 110 extending therebetween. Sidewall 110 has an exterior surface 113 and an interior surface 114. Interior surface 114 defines a substantially cylindrical chamber 115 adapted to receive air/water tip 20 as shown in FIG. 3B.

Chamber 115 can have any size and shape that enables it to receive air/water tip 20. The embodiment of the coupling adaptor shown in FIGS. 3A–3C depicts a chamber having a circular cross-section since air/water tip 20 has a cylindrical shape. The chamber 115 may have any suitable length, but is advantageously sufficiently long to enable it to receive an angled distal end 24 of air/water tip 20 and at least part of a straight portion 22 of the air/water tip 20. The length of chamber 115 may, for example, be about 4.5 cm. Other features of chamber 115 and alternative embodiments are described below in detail.

Coupling adaptor 100 further includes a grasping handle 120, which is an annular flange extending radially and perpendicularly outward from sidewall 110 at proximal grasping end 111 of coupling adaptor 100. Grasping handle 120 is disposed around an opening 112, which has the same diameter as chamber 115. Grasping handle 120 is an example of means for grasping the coupling adaptor such that a user's fingers can grasp the coupling adaptor 100.

A radial extension 118 extends inwardly and integrally from sidewall 110 at distal coupling end 119 to define an exit port 132. Exit port 132 of chamber 115 opens into a channel 133 within an exit tube 130 that terminates with a delivery outlet 134. Exit port 132 is the opening into channel 133 which enables channel 133 to communicate with chamber 115. Note that channel 133 is created by the interior surface of tapered exit tube 130.

Surrounding exit tube 130 is an attachment sleeve 136 extending integrally from sidewall 110. Attachment sleeve 136 has an interior surface 137 with engagement threads 138 positioned thereon. A nozzle or delivery tip 30, shown in FIGS. 3A and 3B, may be selectively attached to coupling adaptor 100 by coupling with threads 138. A variety of tips are available which may be attached such that channel 133 of exit tube 130 is in fluid communication with the tip for guided delivery of the air, water or air/water mixture to a desired location.

Delivery tip 30, as shown in FIG. 3A, is configured to selectively attach in fluid communication with exit port 132. To accomplish this end, delivery tip 30 has a threaded rim 36 that engages threads 138 on the interior surface 137 of attachment sleeve 136. FIG. 3B depicts delivery tip 30 coupled in a threaded engagement with coupling adaptor 100. Delivery tip 30 has a hollow hub 32 with a small bore cannula or nozzle shown at 34 extending from the hub 32 for guiding delivery of a fluid to a desired location. It is, of course, envisioned that different sizes and shapes of spouts 34 can be used depending on the type and intended use of the fluid being delivered.

In alternative embodiments, the delivery tip may be attached to the coupling adaptor by features other than threads. In another alternative embodiment, the delivery tip may be an integral component of the coupling adaptor.

As mentioned above in reference to FIG. 3B, chamber 115 is sufficiently long to enable it to receive the angled distal end 24 of air/water tip 20 and at least part of the straight portion 22 of air/water tip 20. Note that sidewall 110 is sufficiently flexible so that it can advantageously bend in response to a curvature or bend 23 of air/water tip 20. The desired degree of sidewall flexibility may be achieved by selecting a suitably plastic material, by the thickness of the sidewall and/or by combinations thereof. A preferred plastic material is polyethylene as it is flexible. Tougher materials such as polypropylene or nylon may also be used, although, it may be necessary to decrease the thickness of the sidewall as compared with coupling adapters formed from polyethylene to maintain adequate flexibility. The combination of the flexibility of sidewall 110 and the length of chamber 115 enables coupling adaptor 100 to be securely held on air/water tip 20. More particularly, the coupling adaptor is securely positioned on air/water tip 20 due to a chamber that is long enough to receive angled distal end 24 of air/water tip 20 and at least a portion of the straight portion 22 of air/water tip 20 in combination with a sidewall that is sufficiently flexible to bend in response to the angle between the straight portion 22 and the angled distal end 24 of air/water tip 20.

Sidewall 110 may be designed such that its interior surface 114 has a sufficiently close tolerance with air/water tip 20 that there is a seal between chamber 115 and air/water tip 20 along at least a portion of the interface between the interior surface 114 of sidewall 110 and air/water tip 20. Such a seal may be augmented by the curvature of sidewall 110 at the bend 23 in air/water tip 20. The ability of the interior surface 114 to form a seal with air/water tip 20 is enhanced when coupling adaptor 100 is formed from polyethylene since polyethylene has a waxy characteristic. For this additional reason, polyethylene is a preferred plastic material.

While a seal may be formed by reliance on features such as close tolerance, flexibility and length of the sidewall, and the use of polyethylene, sidewall 110 preferably is adapted such that its interior surface 114 forms a secure seal with air/water adaptor. Such a seal may be formed through designing sidewall 110 such that its interior surface has a taper from its proximal end to its distal end. Stated otherwise, the diameter of chamber 115, at its distal end, may be smaller than at its proximal end. While the taper may range up to 10%, it typically ranges from about 3% to about 5%. For example, the diameter of the interior surface of sidewall 110 at its proximal end may be 0.155 inch and the diameter at its distal end may be 0.152 inch, 0.147 inch, 0.145 inch or 0.130 inch such that the distal end diameter is respectively 98%, 95%, 94 or 84% of the proximal end diameter. Other embodiments achieve similar or superior results with different configurations as described below in reference to FIGS. 4A–4B and to FIG. 5.

Figures 4A, 4B:
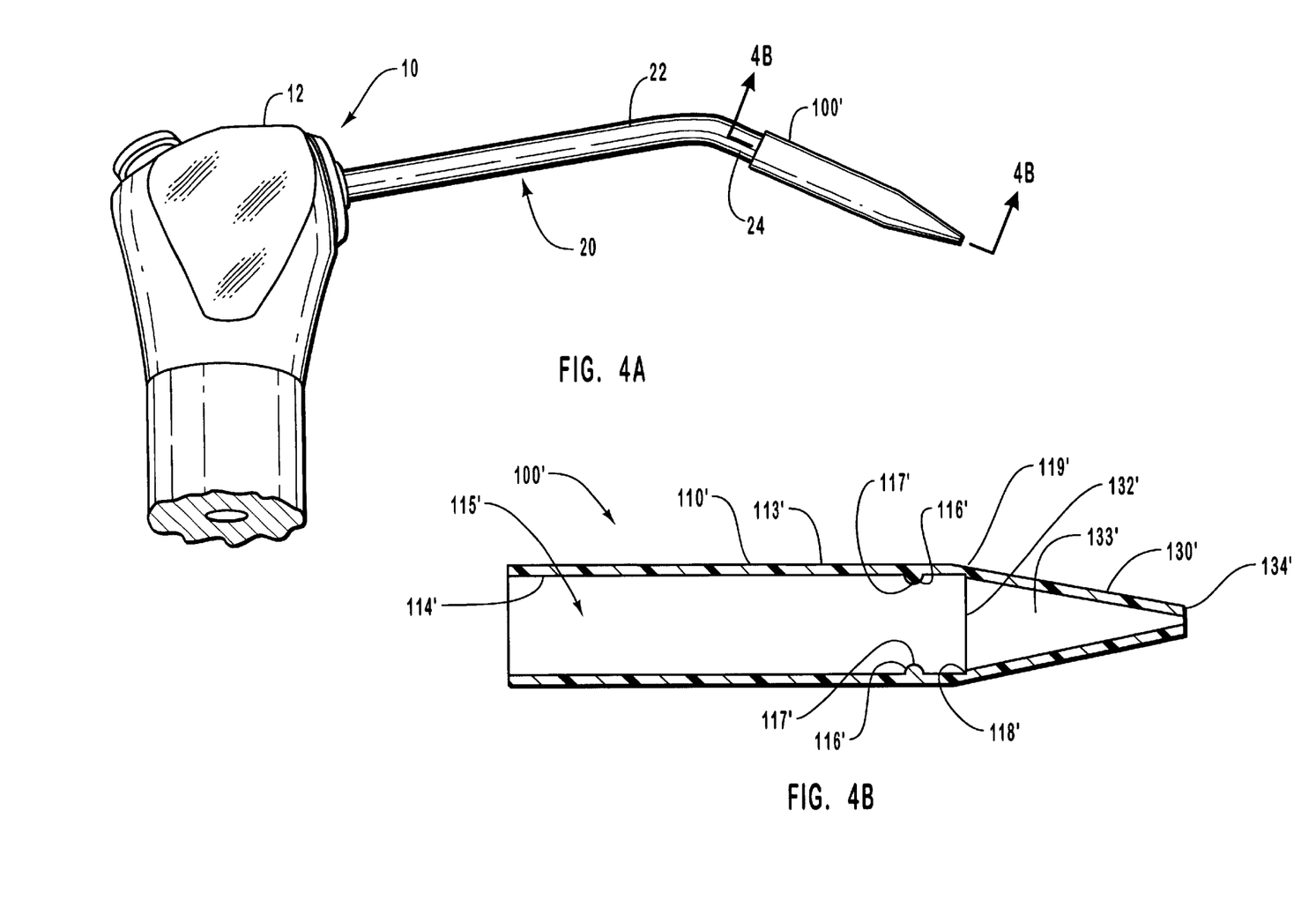
FIG. 4A is a perspective view of an alternative coupling adaptor positioned on an air/water tip.
FIG. 4B is a cross-section view of the coupling adaptor of FIG. 4A taken along line 4B—4B depicting a radial bump extending radially inward from an interior surface of a sidewall of the coupling adaptor.
Figures 5A, 5B:
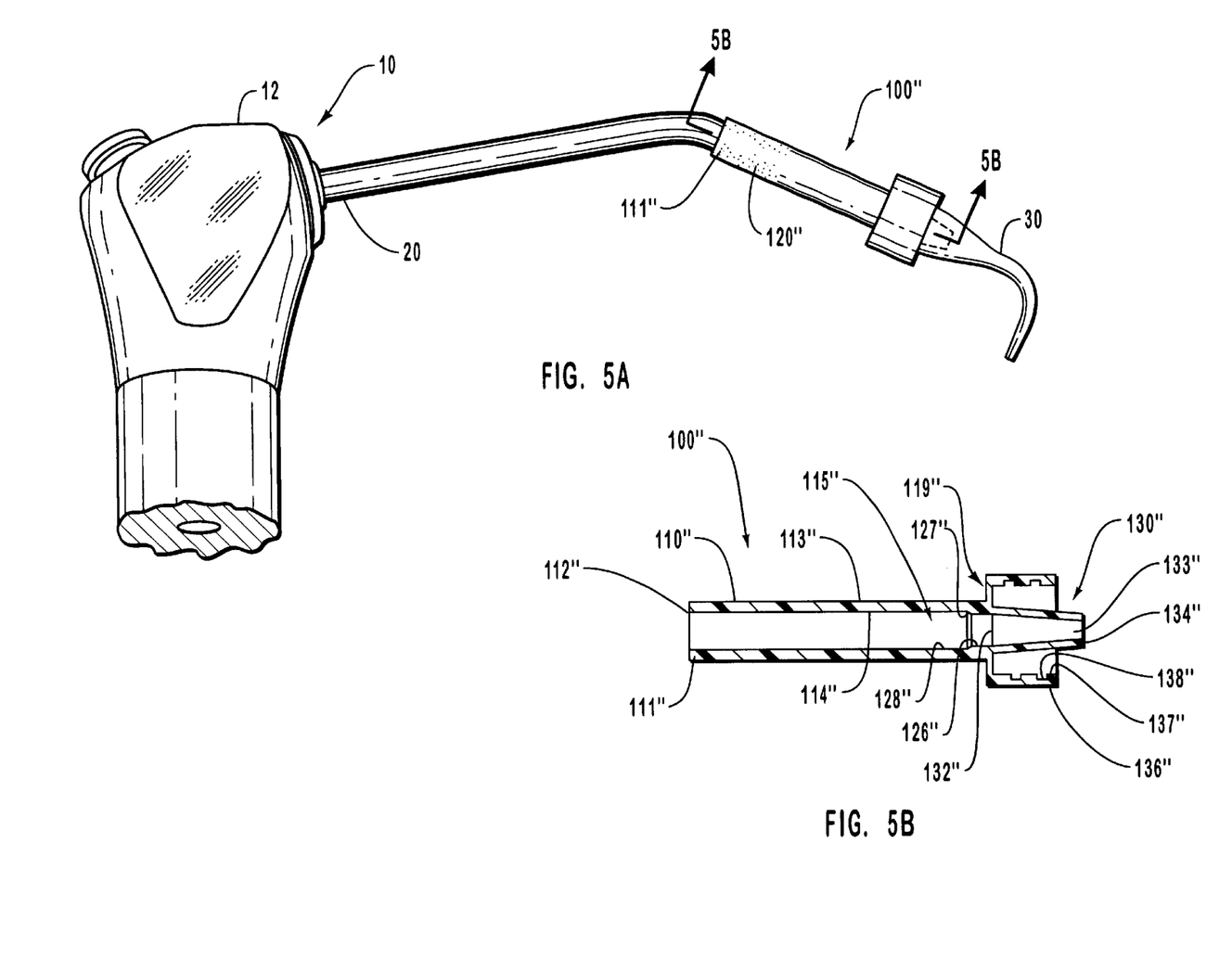
FIG. 5A is a perspective view of an alternative coupling adaptor positioned on an air/water tip and coupled at a distal end with an endodontic irrigator tip.
FIG. 5B is a cross-section view of the coupling adaptor of FIG. 5A taken along line 5B—5B depicting a neck portion extending radially inward from an interior surface of a sidewall of the coupling adaptor and a transitioning shoulder between the neck portion and a body portion.

The alternative embodiment of a coupling adaptor shown in FIGS. 4A–4B is identified at 100'. As shown in FIG. 4B, coupling adaptor 100' has a sidewall 110' with an interior surface 114' that has a radial bump 116' extending radially inward at a distal end of sidewall 110'. The percentage of difference between the diameter at the top 117' of radial bump 116' and the diameter of the interior surface of sidewall 110 at its proximal end may be the same as those described above in reference to the opposing ends of chamber 115. Accordingly, the diameter at the top 117' of radial bump 116' may, for example, be 98%, 95%, 94, 84%, etc. of the proximal end diameter of interior surface 114' of sidewall 110'. In any event, the diameter at the top 117' of radial bump 116' is sufficiently smaller than the remainder of the interior surface of the sidewall 110 that a tight seal with an end 24 of air/water tip 20 is formed at the top 117' of radial bump 116'. Since radial bump 116' is preferably at the distal end of sidewall 110', air/water tip 20 is easily inserted into chamber 115' until reaching radial bump 116'. Upon reaching radial bump 116', more force is required to advance air/water tip 20 into chamber 15. During insertion, air/water tip 20 slides past radial bump 116' until reaching a radial extension 118' of adapter 100'.

A distinction between coupling adaptor 100' and coupling adaptor 100 is that coupling adaptor 100' is significantly shorter than coupling adaptor 100. Note that coupling adaptor 100' is positioned only over angled distal end 24 of air/water tip 20. An advantage of this design is that less material is required to manufacture coupling adaptor 100'. However, since coupling adaptor 100' is shorter and is not anchored onto part of the straight portion 22 of air/water tip 20, the seal between coupling adaptor 100' and air/water tip 20 may need to be stronger than the seal between coupling adaptor 100 and air/water tip 20.

An additional difference between coupling adaptor 100 and coupling adaptor 100' is that coupling adaptor 100' is adapted so as to engage a delivery tip (not shown) with a Luer taper fit instead of a threaded engagement. Accordingly, coupling adaptor 100' has an exit tube 130' that has a more pronounced taper than does exit tube 130. Of course, exit tube 130' may have any suitable length and taper, and advantageously includes a taper that enables it to engage in a compression fit with a delivery tip (not shown). Nevertheless, the exit tube 130' may be modified so as to have mechanical locking elements that engage mechanical locking elements of a delivery tip. As shown, coupling adaptor 100' does not have an attachment sleeve like attachment sleeve 136 of adapter 100 so that exit tube 130' is not radially inset like exit tube 130. Like the threaded engagement of threaded rim 36 of delivery tip 30 with threads 138 on the interior surface 137 of attachment sleeve 136, the compression engagement of the luer taper fit between exit tube 130' and delivery tip 30 is another example of means for securely engaging a delivery tip together with the coupling adaptor.

Radial extension 118' at distal coupling end 119' extends radially inward just barely enough to provide a stop for air/water tip 20 and to define an exit port 132'. Like the corresponding features in coupling adaptor 100, exit port 132' of the chamber provides an opening into channel 133' in exit tube 130' that terminates at a delivery outlet 134'.

FIGS. 5A–5B depicts another embodiment of a coupling adaptor, namely adaptor 100". Like coupling adaptor 100', coupling adaptor 100" has a length that is shorter than that of coupling adaptor 100. More particularly, the chamber 115" is adapted to receive only angled distal end 24 of air/water tip 20.

As shown in FIG. 5B, coupling adaptor 100" has a sidewall 110" with an interior surface 114" adapted such that there is a transitional shoulder portion 127" between a neck portion 126" and a body portion 128". Neck portion 126" has a smaller diameter than body portion 128" to enable a tighter seal to be formed between neck portion 126" and air/water tip 20 than there is between body portion 128" and air/water tip 20. The neck portion 126", transitional shoulder portion 127" and the body portion 128" may have any suitable lengths. Additionally, the transitional shoulder portion 127" may define various angles with the neck portion 126" and the body portion 128". The transitional shoulder 127" may be perpendicular relative to the neck portion 126" and the body portion 128" or oblique as shown.

Note that instead of a grasping a handle such as grasping handle 120, coupling adaptor 100" has a textured engagement surface 120" (FIG. 5A) at its proximal grasping end 111". While grasping handle 120 does not extend perpendicularly from sidewall 110 with a significant length, it may potentially block a portion of the user's view. Since textured engagement surface 120" is flush with the sidewall 110", it provides optimal visibility to the delivery site such that the user's view is not blocked. The engagement surface 120" may be textured by any suitable method.

Figures 6A, 6B:
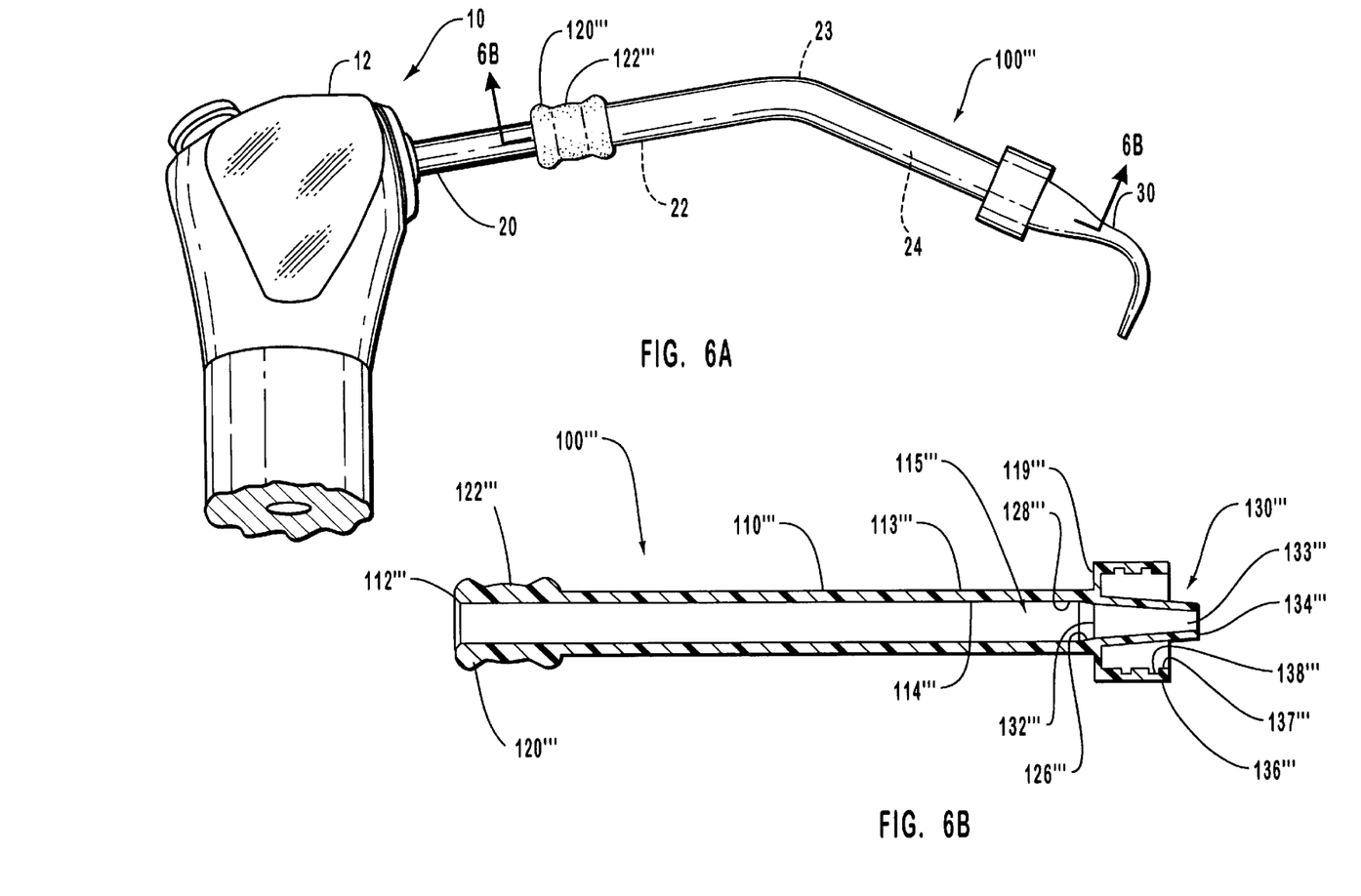
FIG. 6A is a perspective view of an alternative coupling adaptor positioned on an air/water tip and coupled at a distal end with an endodontic irrigator tip.
FIG. 6B is a cross-section view of the coupling adaptor of FIG. 6A taken along line 6B—6B depicting an interior surface of a sidewall of the coupling adaptor having a proximal body portion and a distal neck portion that have different tapers.

FIGS. 6A–6B depict another embodiment of a coupling adaptor, namely adaptor 100'''. Coupling adaptor 100''' has a distal coupling end 119''' that is configured like distal end 119 of adaptor 100. Additionally, coupling adaptor 100''' has the same length as coupling adaptor 100.

Coupling adaptor 100''' has a raised engagement surface 120''' that has an annual dimple 122''' or concavity. Raised engagement surface 120''', textured engagement surface 120" and grasping handle 120 are all examples of means for grasping a coupling adaptor to position the coupling adaptor on an air/water tip and for removal from an air/water tip. As shown, the grasping handle 120 and the alternative grasping surfaces 120" and 120''' are located at the proximal grasping end of the coupling adaptor. While the grasping handle or grasping surface may also be located elsewhere on the coupling adaptor, the location at proximal grasping end 111 is the least likely to result in interference with the user's vision of the delivery site. While the examples of the grasping means are highly useful, the proximal grasping end may be merely the terminal end of the coupling adaptor that has the same texture, shape and profile as the remainder of the coupling adaptor.

As shown in FIG. 6B, there is no transitional shoulder since the body portion 128''' tapers toward neck portion 126''' such that the neck portion 126''' and the body portion 128''' are merely sections with different tapers. Neck portion 126''' has a smaller diameter along its length than does body portion 128''' to enable a tighter seal to be formed between neck portion 126''' and air/water tip 20 than there is between body portion 128''' and air/water tip 20. The neck portion 126''' and the body portion 128''' may have any suitable lengths. For example, instead of a neck portion 126''' at only the distal end of sidewall 110''', the neck portion 126''' may extend to bend 23 such that body portion 128''' corresponds with straight portion 22 of air/water tip 20. Additionally, the neck portion 126''' and the body portion 128''' may have any suitable taper such as those described above in reference to coupling adaptor 100. For example, like body portion 128", body portion 128''' may not have any taper along its length while neck portion 126''' has a taper that enables it form a tight seal with air/water tip 20.

Note that like coupling adaptor 100, coupling adaptor 100''' has a chamber 115''' that is long enough to receive angled distal end 24 of air/water tip 20 and at least part of the straight portion 22 of air/water tip 20. Also like coupling adaptor 100, coupling adaptor 100''' has a sidewall 110''' with sufficient flexibility to bend in response to the angle between the straight portion 22 and the angled distal end 24 of air/water tip 20. As discussed above, the combination of the length and the flexibility of such a sidewall enables coupling adaptor 100''' to be securely held on air/water tip 20 to form a seal. The taper of neck portion 126''' further increases the strength of the seal.

There are several features that enable the coupling adaptor to securely remain on the air/water tip once the air/water tip is positioned in the chamber. Manufacturing the coupling adaptor from polyethylene is an example of a feature that ensures that the coupling adaptor is secured on the air/water tip. Another feature is the combination of a long and flexible sidewall. More particularly, a sidewall that is sufficiently long to enable the chamber to receive an angled distal end of the air/water tip and at least part of a straight portion of the air/water tip, and a flexible sidewall. The sidewall is sufficiently flexible to bend in response to an angle between the straight portion and an angled distal end of the air/water tip once the air/water tip is inserted into the chamber of the coupling adaptor such that the angled distal end of the air/water tip reaches a proximal end of the chamber.

Other features that enable the coupling adaptor to securely remain on the air/water tip once the air/water tip is positioned in the chamber are also examples of means for forming a seal with the air/water tip once the air/water tip is positioned in the chamber. An example of such a seal forming means is provided by an interior surface of the sidewall that has a taper along at least a portion of the length of the sidewall such that the diameter of the chamber at the proximal grasping end is larger than at the opposing distal coupling end. Another example of such a seal forming means is provided by an interior surface of the sidewall that has a radial bump extending radially inward such that the diameter of the chamber at the radial bump is the smallest along the length of the chamber. Yet another example of a seal forming means is provided by an interior surface of the sidewall that has a neck portion and a body portion, wherein the diameter of the chamber at the neck portion is smaller than at the body portion. The neck portion and the body portion may adjacent to each other or be separated by a transitional shoulder portion.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Letters Patent is:

1. A coupling adaptor for positioning on an air/water tip of a fluid dispensing device such as a three-way syringe to enable a delivery tip to be coupled in fluid communication with the air/water tip, the coupling adaptor comprising:

a sidewall extending between a proximal grasping end and an opposing distal coupling end, the sidewall having an interior surface defining a chamber with an opening at the proximal grasping end sized to enable an air/water tip to be inserted into the chamber and having an exit port at the distal coupling end, the sidewall being adapted to enable the coupling adaptor to securely remain on the air/water tip once the air/water tip is positioned in the chamber, an exit tube extending integrally from the sidewall at the distal coupling end of the sidewall, and wherein the exit port of the chamber provides an opening into a channel in the exit tube that terminates at a delivery outlet, wherein the exit tube is adapted to couple with a delivery tip such that the delivery tip can be coupled to the coupling adaptor and be in fluid communication with the air/water tip positioned in the chamber, such that fluid flowing out of the air/water tip can flow into the delivery tip.

2. A coupling adaptor as recited in claim 1, wherein the coupling adaptor is formed from polyethylene.

3. A coupling adaptor as recited in claim 1, wherein the coupling adaptor is formed from at least one of polypropylene or nylon.

4. A coupling adaptor as recited in claim 1, wherein the chamber is sufficiently long to enable it to receive an angled distal end of the air/water tip and at least part of a straight portion of the air/water tip, and wherein the sidewall is sufficiently flexible to bend in response to an angle between the straight portion and the angled distal end of the air/water tip once the air/water tip is fully inserted into the chamber of the coupling adaptor.

5. A coupling adaptor as recited in claim 1, wherein the interior surface of the sidewall has a taper along at least a portion of the length of the sidewall such that the diameter of the chamber at the proximal grasping end is larger than at the opposing distal coupling end.

6. A coupling adaptor as recited in claim 1, wherein the interior surface of the sidewall has a radial bump extending radially inward such that the diameter of the chamber at the radial bump is the smallest along the length of the chamber.

7. A coupling adaptor as recited in claim 1, wherein the interior surface of the sidewall has a neck portion and a body portion and wherein the diameter of the chamber at the neck portion is smaller than at the body portion.

8. A coupling adaptor as recited in claim 1, further comprising an attachment sleeve extend integrally from the sidewall around the exit tube, the attachment sleeve having an interior surface with engagement threads for threaded coupling with the delivery tip.

9. A coupling adaptor as recited in claim 1, wherein the exit tube is configured to be coupled with the delivery tip in a compression fit.

10. A coupling adaptor as recited in claim 1, further comprising means for grasping the coupling adaptor, the grasping means being located at the proximal grasping end of the coupling adaptor.

11. A coupling adaptor as recited in claim 10, wherein the grasping means includes at least one of a grasping handle or a textured surface disposed at or near the grasping end.

12. A coupling adaptor for positioning on an air/water tip of a fluid dispensing device such as a three-way syringe to enable a delivery tip to be coupled in fluid communication with the air/water tip, the coupling adaptor comprising:

a sidewall extending between a proximal grasping end and an opposing distal coupling end, the sidewall having an interior surface defining a chamber with an opening at the proximal grasping end sized to enable an air/water tip to be positioned in the chamber and having an exit port at the distal coupling end, wherein the chamber is sized to enable the coupling adaptor to securely remain on the air/water tip once the air/water tip is positioned in the chamber;

means within the interior surface of the sidewall for forming a seal with the air/water tip once the air/water tip is positioned in the chamber; and an exit tube extending integrally from the sidewall at the distal coupling end of the sidewall, wherein the exit port of the chamber provides an opening into a channel in the exit tube that terminates at a delivery outlet, wherein the exit tube is adapted to couple with a delivery tip such that the delivery tip can be coupled to the coupling adaptor and be in fluid communication with the air/water tip positioned in the chamber.

13. A coupling adaptor as recited in claim 12, wherein the coupling adaptor is formed from, at least one of polyethylene, polypropylene or nylon.

14. A coupling adaptor as recited in claim 12, wherein the chamber is sufficiently long to enable it to receive an angled distal end of the air/water tip and at least part of a straight portion of the air/water tip, and wherein the sidewall is sufficiently flexible to bend in response to an angle between the straight portion and the angled distal end of the air/water tip once the air/water tip is fully inserted into the chamber of the coupling adaptor.

15. A coupling adaptor as recited in claim 12, wherein the seal forming means is a taper along at least a portion of the length of the sidewall such that the diameter of the chamber at the proximal grasping end is larger than at the opposing distal coupling end.

16. A coupling adaptor as recited in claim 12, wherein the seal forming means is a radial bump extending radially inward such that the diameter of the chamber at the radial bump is the smallest along the length of the chamber.

17. A coupling adaptor as recited in claim 12, wherein the seal forming means is a neck portion of the interior surface of the sidewall sized such that the diameter of the chamber is smaller at the neck portion than at a body portion of the interior surface of the sidewall.

18. A coupling adaptor as recited in claim 12, further comprising an attachment sleeve extending integrally from the sidewall around the exit tube, the attachment sleeve having an interior surface with engagement threads for threaded coupling with the delivery tip.

19. A coupling adaptor as recited in claim 12, wherein the exit tube is configured to be coupled with the delivery tip in a compression fit.

20. A coupling adaptor as recited in claim 12, further comprising means for grasping the coupling adaptor, the grasping means being located at the proximal grasping end of the coupling adaptor and being at least one of a grasping handle or a textured surface.

21. A coupling adaptor for positioning on an air/water tip of a fluid dispensing device such as a three-way syringe to enable a delivery tip to be coupled in fluid communication with the air/water tip, the coupling adaptor comprising:

a sidewall extending between a proximal grasping end and an opposing distal coupling end, the sidewall having an interior surface defining a chamber with an opening at the proximal grasping end sized to enable an air/water tip to be positioned in the chamber and having an exit port at the distal coupling end, wherein the chamber is sized to enable the coupling adaptor to securely remain on the air/water tip once the air/water tip is positioned in the chamber, wherein the interior surface of the sidewall is adapted to form a seal with the air/water tip once the air/water tip is positioned in the chamber;

an exit tube extending integrally from the sidewall at the distal coupling end of the sidewall, wherein the exit port of the chamber provides an opening into a channel in the exit tube that terminates at a delivery outlet, wherein the exit tube is adapted to couple with a delivery tip such that the delivery tip can be coupled to the coupling adaptor and be in fluid communication with the air/water tip positioned in the chamber; and an attachment sleeve extending integrally from the sidewall around the exit tube, the attachment sleeve having an interior surface with engagement threads for threadably coupling with the delivery tip.

* * * * *

UNITED STATES PATENT AND TRADEMARK OFFICE
CERTIFICATE OF CORRECTION

PATENT NO. : 6,510,970 B2
DATED : January 28, 2003
INVENTOR(S) : Bruce S. McLean, Wade J. Cannon and Dan E. Fischer It is certified that error appears in the above-identified patent and that said Letters Patent is hereby corrected as shown below:

Title page,
Item [56], References Cited, U.S. PATENT DOCUMENTS, change "Dragon" to -- Dragan --; and change "5,767,759" to -- 5,765,759 --

Column 5,
Line 27, after "94" insert -- % --
Line 41, after "94" insert -- % --

Column 7,
Line 28, after "it" insert -- to --

Column 8,
Line 8, after "may" insert -- be --

Column 9,
Line 4, change "extend" to -- extending --

Signed and Sealed this

Twenty-ninth Day of June, 2004

JON W. DUDAS
*Acting Director of the United States Patent and Trademark Office*